United States Patent

Huang

[11] Patent Number: 5,705,729
[45] Date of Patent: Jan. 6, 1998

[54] ISOPARAFFIN-OLEFIN ALKYLATION PROCESS

[75] Inventor: Tracy J. Huang, Lawrenceville, N.J.

[73] Assignee: Mobil Oil Corporation, Fairfax, Va.

[21] Appl. No.: 561,643

[22] Filed: Nov. 22, 1995

[51] Int. Cl.$^6$ ................... C07C 2/58; C07C 2/56
[52] U.S. Cl. ................ 585/722; 585/709; 585/721
[58] Field of Search .................. 585/722, 721, 585/709

[56] References Cited

U.S. PATENT DOCUMENTS

| | | | |
|---|---|---|---|
| 3,236,671 | 2/1966 | Dybalski et al. | 106/277 |
| 3,251,902 | 5/1966 | Garwood et al. | 260/683.64 |
| 3,450,644 | 6/1969 | Lanewala et al. | 252/416 |
| 3,549,557 | 12/1970 | Bolton et al. | 252/455 |
| 3,624,173 | 11/1971 | Kirsch et al. | 260/671 |
| 3,644,565 | 2/1972 | Biale et al. | 260/683.43 |
| 3,647,916 | 3/1972 | Caesar et al. | 260/683.43 |
| 3,655,813 | 4/1972 | Kirsch et al. | 260/683.43 |
| 3,706,814 | 12/1972 | Kirsch et al. | 260/683.43 |
| 3,738,977 | 6/1973 | Biale et al. | 260/94.9 |
| 3,865,894 | 2/1975 | Kirsch et al. | 260/683.43 |
| 3,893,942 | 7/1975 | Yang | 252/411 |
| 3,917,738 | 11/1975 | Fenske et al. | 260/683.43 |
| 4,008,291 | 2/1977 | Zabransky et al. | 260/683.43 |
| 4,377,721 | 3/1983 | Chester et al. | 585/722 |
| 4,384,161 | 5/1983 | Huang | 585/722 |
| 4,922,615 | 5/1990 | Nishida | 30/360 |
| 5,012,033 | 4/1991 | Child et al. | 585/722 |
| 5,073,665 | 12/1991 | Child et al. | 585/722 |
| 5,254,792 | 10/1993 | Husain et al. | 585/722 |
| 5,258,569 | 11/1993 | Chu et al. | 585/722 |
| 5,292,981 | 3/1994 | Huang et al. | 585/722 |

*Primary Examiner*—Glenn Caldarola
*Assistant Examiner*—In Suk Bullock
*Attorney, Agent, or Firm*—Malcolm D. Keen; Thomas W. Steinberg

[57] ABSTRACT

An improved process for alkylation of isoparaffins with olefins to yield a product which includes a high proportion of highly branched alkylates for blending into gasolines is disclosed. The catalyst comprises a large pore zeolite such as USY which may be partially or fully exchanged with a cation or cations selected from the rare-earth metals.

10 Claims, 1 Drawing Sheet

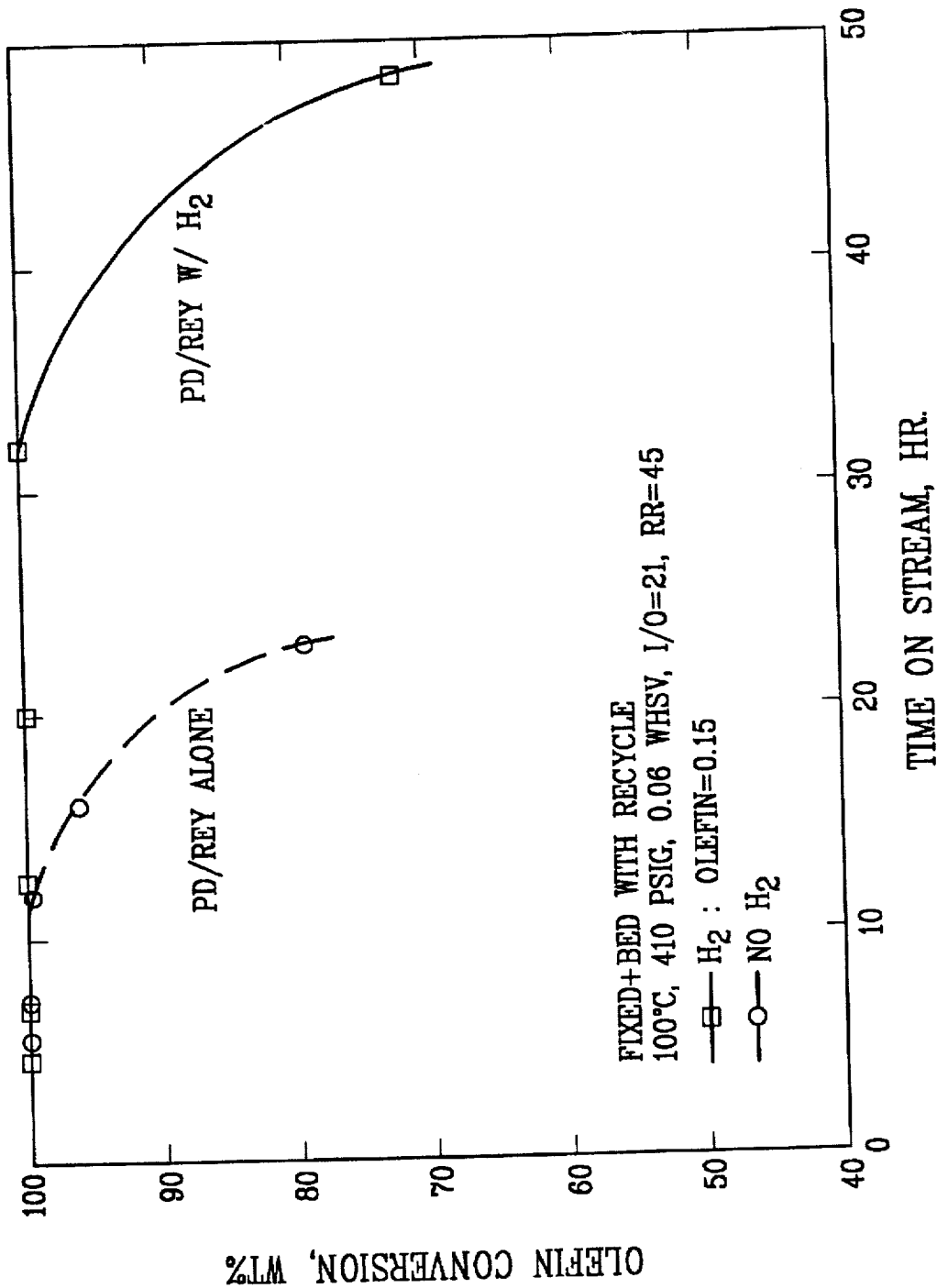

1

ISOPARAFFIN-OLEFIN ALKYLATION PROCESS

FIELD OF THE INVENTION

The instant invention relates to an isoparaffin-olefin alkylation process which is carried out in the presence of a controlled amount of hydrogen and a large pore zeolite catalyst. The alkylate product is useful, inter alia, as an octane enhancer for gasoline. The catalyst comprises a hydrogenation component, and may be partially or fully exchanged with a cation or cations selected from the rare-earth metals.

BACKGROUND OF THE INVENTION

As a result of the curtailment in the use of tetraethyl lead as an octane-improving additive for gasoline, not only has the production of unleaded gasoline increased but the octane number specification of all grades of gasoline has increased as well. Isoparaffin-olefin alkylation is a key route to the production of highly branched paraffin octane enhancers which are to be blended into gasoline.

Alkylation involves the addition of an alkyl group to an organic molecule. Thus, an isoparaffin can be reacted with an olefin to provide an isoparaffin of higher molecular weight. Industrially, alkylation often involves the reaction of $C_2$–$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88–94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alkylation process based on a solid catalyst system. The catalyst of the present invention offers a refiner a more environmentally acceptable alkylation process than the currently used hydrofluoric and sulfuric acid alkylation processes.

Crystalline metallosilicates, or zeolites, have been widely investigated for use in the catalysis of isoparaffin-olefin alkylation. For example, U.S. Pat. No. 3,251,902 describes the use of a fixed bed of ion-exchanged crystalline aluminosilicate having a reduced number of available acid sites for the liquid phase alkylation of $C_4$–$C_{20}$ branched-chain paraffins with $C_2$–$C_{12}$ olefins. The patent further discloses that the $C_4$–$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$–$C_3$ olefins using certain crystalline aluminosilicate zeolite catalysts in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin-olefin alkylation process employing, as catalyst, a Group VIII metal-containing zeolite which is periodically hydrogenated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite catalyzed isoparaffin-olefin alkylation process and further provides for the addition of $C_5$+ paraffins such as Udex raffinate or $C_5$+ olefins to the alkylation reactor feed and the use of specific reactant proportions, halide adjuvants, etc. U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalyst having been pretreated with hydrogen.

U.S. Pat. No. 3,865,894 describes the alkylation of $C_4$–$C_9$ monoolefin employing a substantially anhydrous acidic zeolite, for example acidic zeolite Y (zeolite HY), and a halide adjuvant.

U.S. Pat. No. 3,917,738 describes a process for alkylating an isoparaffin with an olefin using a solid, particulate catalyst capable of adsorbing the olefin. The isoparaffin with an olefin using a solid, particulate catalyst capable of adsorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,377,721 describes an isoparaffin-olefin alkylation process utilizing, as catalyst, ZSM-20, preferably HZSM-20 or rare earth cation-exchanged ZSM-20.

U.S. Pat. No. 4,384,161 describes a process of alkylating isoparaffins with olefins to provide alkylate employing as catalyst a large pore zeolite capable of adsorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

U.S. Pat. Nos. 4,992,615; 5,012,033; and 5,073,665 describe an isoparaffin-olefin alkylation process utilizing, as a catalyst, a zeolite designated as MCM-22. U.S. Pat. Nos. 5,258,569 and 5,254,792 disclose isoparaffin olefin alkylation processes which utilize MCM-36 and MCM-49 respectively, as catalysts.

U.S. Pat. No. 4,008,291 discloses a moving bed alkylation process in which hydrogen is added to a catalyst reactivation zone but is not added to the reaction zone itself in a controlled amount, as taught in the instant invention.

U.S. Pat. No. 5,292,981 describes a process for isoparaffin-olefin alkylation in which a slurry of zeolite particles and a feed of liquid reactants comprising isoparaffins and olefins is circulated in a reactor. The isoparaffin/olefin ratio is less than 100/1 in the slurry. A first portion of the slurry is recycled to provide a ratio of at least 500/1. A second portion of the slurry is passed to a separating means wherein alkylate product is separated from the zeolite.

SUMMARY OF THE INVENTION

This invention relates to an improved process of reacting an isoparaffin with olefin molecules in the presence of a composite catalyst comprising a large pore zeolite and a controlled amount of hydrogen. The presence of a controlled amount of hydrogen improves catalyst stability and alkylate quality. The alkylation of isobutane with light olefins is important in the manufacture of high octane gasoline blending stocks. Alkylate typically comprises 10–15% of the gasoline pool. It has high RON and MON, is low in sulfur content, contains no olefins or aromatics, demonstrates excellent stability and is clean burning.

Zeolites with pores sufficiently large enough to adsorb 2,2,4 trimethylpentane, such as faujasite (zeolite X and zeolite Y), ZSM-3,ZSM-4,ZSM-18,ZSM-20, mordenite, MCM-22,MCM-36,MCM-49,MCM-56 and zeolite L are employed as catalysts in the instant invention. The catalysts may be exchanged either partially or fully with rare-earth cations. The zeolites further comprise a hydrogenation component or components such as Pt or Pd. In a preferred embodiment, hydrogen is cofed with isoparaffin and olefin into the alkylation reactor at a hydrogen/olefin ratio of 0.2 to 1. The examples employ isobutane and 2-butene. At 0.2/1, a minimal amount of butene is hydrogenated and the production of $C_5+$ molecules is maximized.

BRIEF DESCRIPTION OF THE DRAWINGS

The FIGURE illustrates the improvement in time on stream for the catalyst as well as in the wt % of olefin conversion when a controlled amount of hydrogen is added to a large pore, rare earth exchanged zeolite comprising a hydrogenation component.

DETAILED DESCRIPTION OF THE INVENTION

Feed

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, pentene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference.

Hydrocarbon streams containing a mixture of paraffins and olefins such as FCC butane/butene stock may also be employed. The isoparaffin/olefin weight ratio in the feed may range from 1:1 to over 1000:1. Although the ratio is usually about 100:1, a ratio of over 500:1 in the reactor is more desirable and a ratio of over 1000:1 is most desirable. A high isoparaffin/olefin ratio may be achieved by recycle of part of the reactor effluent or by back-mixing of the reactor content.

Alkylation Catalyst

The feed, discussed above, is contacted with an alkylation catalyst which comprises a large pore zeolite, in the presence of a controlled amount of hydrogen. The catalyst further comprises a hydrogenation component and, optionally, a rare-earth element. The zeolite component is a large-pore zeolite which is capable of adsorbing 2,2,4 trimethylpentane. The pore diameter of the zeolite is larger than 6 Å, preferably larger than 7 Å. Large pore zeolites include the faujasites, such as zeolite X, zeolite Y, and USY.Zeolite X is described more fully in U.S. Pat. No. 2,882,244. For purposes of this invention, zeolite Y includes zeolite Y in its as synthesized form, as well as its variant forms including framework dealuminated zeolite Y, e.g. ultrastable Y (USY), described in U.S. Pat. No. 3,293,192 and LZ-210 described in U.S. Pat. No. 4,503,023. Other suitable zeolites include ZSM-3 (described in U.S. Pat. No. 3,415,736), ZSM-4 (more fully described in U.S. Pat. Nos. 4,021,947 and 4,091,007), ZSM-20(described in U.S. Pat. No. 3,972,983), mordenite (described in U.S. Pat. Nos. 5,219,547 and 5,211, 935),MCM-22(described in U.S. Pat. Nos. 5,073,665 and 5,105,054), MCM-36(described in U.S. Pat. No. 5,310,715 and 5,296,428), MCM-49(described in U.S. Pat. No. 5,236, 575), MCM-56(described in U.S. Pat. No. 5,362,697), zeolite-L(described in U.S. Pat. Nos. 4,908,342 and 5,063, 038), zeolite beta (described in U.S. Pat. Nos.5,164,170 and 5,160,169). Faujasites are preferred in the instant invention. The entire disclosures of the patents referred to in this paragraph are expressly incorporated by reference.

The zeolites are preferably partially or fully exchanged with at least one rare-earth cation, such as cations of lanthanum or cerium. Mixtures of rare-earth cations may also be used.

The present catalyst can be used in intimate combination with one or more hydrogenating components such as these selected from the Group VIII metals (such as Co, Ni, Fe, Ru, Pd and Pt) or other transition metals (such as Cr, Mo, W, Cu, Zn, Ga, Sn and Ti). Noble metals are employed particularly when a hydrogenation-dehydrogenation function is desired. Such components can be associated chemically and/or physically with the catalyst. Thus, the hydrogenating component can be introduced into the catalyst composition by way of co-crystallization, exchanged into the composition to the extent a Group IIA element, e.g., aluminum, is in the structure, impregnated therein or intimately physically admixed therewith. Such component can be impregnated in, or on, the catalyst such as, for example, by, in the case of platinum, treating the catalyst with a solution containing the platinum metal-containing ion. Thus, suitable platinum compounds for this purpose include chloroplatinic acid, platinous chloride and various compounds containing the platinum amine complex.

The catalyst of the invention must undergo thermal treatment if rare earth cations are used in combination with noble metals. This thermal treatment is generally performed by heating the catalyst at a temperature of at least about 370° C., usually in the range from 400° C.–600° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use as an alkylation catalyst in the process of this invention, the catalyst must be at least partially dehydrated. This dehydration can be accomplished by heating the catalyst to a temperature in the range of from about 200° C., to about 595° C., in an atmosphere such as air, nitrogen, etc., and at atmospheric, subatmospheric or superatmospheric pressures for a period of from between about 30 minutes to about 48 hours. Dehydration can also be performed at room temperature merely by placing the catalyst in a vacuum but a longer time will be required to achieve a suitable degree of dehydration. Prior to alkylation the catalyst is reduced with hydrogen and reduced.

The catalyst can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It is desired to incorporate the catalytically active catalyst crystalline material with another material, i.e., a binder, which is resistant to the temperatures and other conditions employed in the isoparaffin alkylation process of this invention. Suitable binder materials include active and inactive materials such as clays, silica and/or metal oxides such as alumina. These can be either naturally occurring or provided in the form of gelatinous precipitates or gels including mixtures of silica and metal oxides. Use of a binder material in conjunction with the catalytically active crystalline material, i.e., combined therewith, which itself is catalytically active may change the conversion and/or selectivity of the catalyst. Inactive materials suitably serve as diluents to control the amount of conversion so that products can be obtained economically and in a controlled fashion without having to employ other means for controlling the rate of reaction. These materials can be incorporated into naturally occurring clays, e.g., bentonite and kaolin, to improve the crush strength of the catalyst under commercial operating conditions. Good crush strength is an advantageous attribute for commercial use since it prevents or delays breaking down of the catalyst into powder-like materials.

Naturally occurring clays which can be composited with the present catalyst crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with catalyst crystals also include inorganic oxides, notably alumina.

The alumina binder may undergo a phase transformation during calcination, whereby the water solubility of the alumina is decreased. The hydroxyl content of the alumina may be decreased by calcination. In particular, calcination may transform the pseudoboehmite form of alumina into gamma-alumina.

Apart from or in addition to the foregoing binder materials, the present catalyst crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may be advantageous to provide at least a part of the foregoing matrix materials in colloidal form so as to facilitate extrusion of the catalyst component(s).

The relative proportions of finely divided catalyst crystals and inorganic oxide matrix can vary widely with the catalyst crystals content ranging from about 1 to about 95 percent by weight and more usually, particularly when the composite is prepared in the form of beads, in the range of about 2 to about 80 weight percent of the composite.

Operating Conditions

The operating temperature of the alkylation process herein can extend over a fairly broad range, e.g., from about 0° C. to about 400° C., and is preferably within the range of from about 50° C., to about 120° C. The practical upper operating temperature will often be dictated by the need to avoid an undue occurrence of undesirable side reactions.

The pressures employed in the present process can extend over a considerably wide range, from subatmospheric pressure to about 2000 psig, and preferably from atmospheric pressure to about 1000 psig. The mole ratio of hydrogen to olefin in the feed is controlled to be less than or equal to 0.2:1.0, preferably 0.15:1.0.

The amount of catalyst used in the present alkylation process can be varied over relatively wide limits. In general, the amount of catalyst as measured by the weight hourly space velocity (WHSV) based on olefin can range from about 0.01 to about 100 hr$^{-1}$. It will, of course, be realized by those skilled in the art that the amount of catalyst selected for a particular reaction will be determined by several variables including the reactants involved as well as the nature of the catalyst and the operating conditions employed.

The isoparaffin reactant used in the present alkylation process may be one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed herein generally contains from 2 to about 12 carbon atoms. Representative examples are ethene, propene, butene-1, butene-2, isobutene, pentenes, hexenes, heptenes and octenes. Particularly preferred are $C_3$ and $C_4$ olefins and mixtures thereof.

In general, the mole ratio of total isoparaffin to total olefin alkylating agent in the combined hydrocarbon feed can be from about 1:2 to about 500:1 and is preferably in the range of from about 5:1 to about 100:1. The isoparaffin and/or olefin reactants can be in the vapor phase, the liquid phase and/or a supercritical state and can be neat, i.e., free from intentional admixture of dilution with other material, or the reactants can be brought into contact with the catalyst composition with the aid of carrier gases or diluents such as, for example, nitrogen.

The alkylation process of the present invention can be carried out as a batch-type, semi-continuous or continuous operation utilizing a fixed bed reactor moving bed reactor or slurry reactor. The catalyst after use, is conducted to a regeneration zone where coke is removed, e.g., by burning in an oxygen-containing atmosphere (such as air) at elevated temperature or by extracting with a solvent, after which the regenerated catalyst is recycled to the conversion zone for further contact with the organic reactants. Particular process configurations and variations may be accrued at by substituting the present catalyst for the catalyst as described in U.S. Pat. Nos. 4,992,615; 5,012,033; and 5,073,665.

The following examples, not intended to be limiting, are included below.

EXAMPLES

The beneficial effect of hydrogen in alkylation of isobutane with butene-2 over rare-earth exchanged Y-zeolite (REHY) was demonstrated in fixed-bed operation with internal recycle in liquid phase at 410 psig and 100° C. with a recycle ratio of 45:1 in a tubular reactor in an up-flow fashion. A gear pump was used for the recycle operation.

EXAMPLE 1

Isobutane/butene-2 alkylation with 0.3% Pd/REHY in the absence of hydrogen.

2.5 grams of REHY catalyst of 30–60 mesh particles were charged to a fixed-bed reactor. The catalyst was calcined in dry air at 400° C. for 3 hours, then purged with $N_2$, reduced with $H_2$ at 120° and 1 atm for one hour, and finally purged with $N_2$ at 120° C. for one hour. After that, the reactor was cooled down to room temperature and the entire reactor/recycle system was filled up with isobutane under pressure. The recycle pump was started at a flow rate of 225 ml/hr and the reactor system was heated to the desired temperature. When the desired operating temperature of 100° C. was reached, a pre-mixed isobutane/butene-2 feed (with an isobutane/butene mole ratio [I/O] of 21:1) containing 1 wt % of n-hexane as an internal standard was continuously fed into the reactor at a rate of 5 ml/hr. Under these conditions, the recycle ratio (RR, defined as the volume ratio of the recycled reactor effluent stream to the fresh feed) was maintained at 45:1. On-line GC samples were taken periodically to monitor olefin conversion, $C_5+$ yield and product distribution. The plot of olefin conversion as a function of time on stream is shown in the FIGURE. Clearly, the cycle length (defined as total time on stream at which olefin conversion was maintained at 100%) was only 12 hours. After that, olefin breakthrough took place and the olefin conversion dropped below 100%. In addition, the ratio of trimethylpentanes to dimethylhexanes (T/D) in the alkylate (a reflection of alkylate octane quality) varied from 3.2 to 3.6 depending on the time on stream.

EXAMPLE 2

Isobutane/butene-2 alkylation with 0.3% Pd/REHY in the presence of a controlled amount of $H_2$ was demonstrated, showing the beneficial effect of $H_2$ addition in a controlled amount.

The same experiment with the same 0.3% Pd/REHY catalyst was conducted as in Example 1 except that the feed was pre-saturated with $H_2$ under a given pressure to give a mole ratio of $H_2$ to butene of 0.15:1.0. This hydrogen containing isobutane/butene feed was continuously pumped into the reactor. The results of olefin conversion, $C_5+$ yield, T/D, degree of hydrogenation and product distribution as a function of time on stream are given below in Table 1. The $C_5+$ yield is defined as grams of $C_5+$ alkylate produced per gram of olefin converted. The plot of olefin conversion vs. time on stream is shown in FIG. 1. Clearly, the presence of the controlled amount of $H_2$ gave a better cycle length (31 hours vs. 12 hours) indicating an improved catalyst stability. In addition, the ratio of trimethylpentanes to dimethylhexanes (T/D) in the alkylate was significantly improved (6.3–7.8 vs. 3.2–3.6 for the alkylation without $H_2$), reflecting a better octane quality for the alkylate product.

TABLE 1

Isobutane/butene-2 Alkylation over Pd/REY with $H_2$
(100° C., 410 psig, 0.06 WHSV, I/O = 21, PR = 45:1 and $H_2$/olefin = 0.15)

| TOS. Hr. (Time on Stream) | 4.5 | 7 | 12.5 | 20 | 31.5 |
|---|---|---|---|---|---|
| $C_4$ = Conv., % | 100 | 100 | 100 | 100 | 99.6 |
| $C_4$ = Hydrogen % | 15 | 15 | 20 | 21 | 15 |
| $C_5+$ Yield (g $C_5+$/g $C_4$ = converted) | 1.79 | 1.85 | 1.70 | 1.63 | 1.84 |
| T/D | 7.8 | 6.8 | 6.8 | 7.2 | 6.3 |
| Product Dist. wt % | | | | | |
| $C_5$–$C_7$ | 15.4 | 23.0 | 31.5 | 30.5 | 22.5 |
| $C_8$ | 84.2 | 75.5 | 66.0 | 65.6 | 64.7 |
| $C_9+$ | 0.4 | 1.5 | 2.5 | 3.9 | 12.8 |

EXAMPLE 3

Isobutane/butene-2 alkylation was demonstrated with 0.3% Pd/REHY in the presence of $H_2$ with various $H_2$ butene ratios. The same experiment with the same 0.3% Pd/REHY catalyst was conducted as in Example 1 except that a hydrogen gas stream was continuously cofed with the isobutane/butene-2 feed stream into the reactor at different flow rates to give different $H_2$ to butene mole ratios (varying from 1.1:1.0 to 0.15:1.0 as shown in Table 2). The results of olefin conversion, $C_5+$ yield, T/D, degree of hydrogenation and product distribution as a function of time on stream are given below in Table 2. At a $H_2$/butene ratio of 1.1:1.0, 100% of butene was hydrogenated. When the ratio was reduced to 0.4:1.0, 40% of butene was hydrogenated. When the ratio was further decreased to 0.2:1.0, only 20% of butene was hydrogenated and the $C_5+$ yield was increased significantly to 1.51. Further reduction of the ratio to 0.15:1.0 resulted in further improvement of the $C_5+$ yield to 1.85. The T/D ratios obtained from the various $H_2$/butene mole ratios in this example were all much better than those obtained from alkylation in the absence of $H_2$ (see Example 1). Thus, the preferred $H_2$/butene mole ratio in the present concept is equal to or less than 0.2:1.0.

TABLE 2

Isobutane/butene-2 Alkylation over 0.3% Pd/REY with Various amount of $H_2$/butene mole ratio
(100° C., 410 psig, 0.06 WHSV. I/O = 21 and RR = 45:1)

| TOS. Hr. (Time on Stream) | 4.5 | 32 | 47 | 53 | 77 | 87 | 4.5* |
|---|---|---|---|---|---|---|---|
| $H_2$:$C_4$ = (mole ratio) | 1.1 | 0.6 | 0.6 | 0.6 | 0.4 | 0.2 | 0.15 |
| $C_4$ = Conv., % | 100 | 100 | 100 | 100 | 100 | 100 | 100 |
| $C_4$ = Hydrogen % | 100 | 62 | 62 | 59 | 40 | 20 | 15 |
| T/D | | 5.6 | 5.9 | 6.0 | 6.2 | 6.6 | 6.8 |
| $C_5+$ Yield | — | 0.79 | 0.81 | 0.79 | 1.37 | 1.51 | 1.85 |
| Product Dist. wt % | | | | | | | |

TABLE 2-continued

Isobutane/butene-2 Alkylation over 0.3% Pd/REY with
Various amount of H₂/butene mole ratio
(100° C., 410 psig, 0.06 WHSV. I/O = 21 and RR = 45:1)

| | | | | | | | |
|---|---|---|---|---|---|---|---|
| C₅–C₇ | — | 25.0 | 24.4 | 23.5 | 29.2 | 28.9 | 23.0 |
| C₈ | — | 74.0 | 74.3 | 74.2 | 67.0 | 63.4 | 75.5 |
| C₉+ | — | 1.0 | 1.3 | 2.3 | 3.8 | 7.7 | 0.4 |

*Data from Example 2 (see Table 1)

I claim:

1. An isoparaffin-olefin alkylation process which comprises reacting isoparaffin and olefin under alkylation conditions in the presence of a catalyst which composes a large pore zeolite having a hydrogenation component, the zeolite being capable of adsorbing 2,2,4-trimethylpentane, and hydrogen in a mole ratio of hydrogen to olefin between 0.4 and 0.15, to provide an alkylate product.

2. The process of claim 1, wherein the mole ratio of hydrogen to olefin is no greater than 0.2:1.

3. The process of claim 1, wherein the mole ratio of hydrogen to olefin is 0.15:1.

4. The process of claim 1, wherein the large pore zeolite is selected from the group consisting of faujasites, zeolite beta, ZSM-3, ZSM-4,ZSM-18,ZSM-20, mordenite, MCM-22, MCM-36, MCM-49, MCM-56 and zeolite L.

5. The process of claim 4, wherein the faujasites are selected from the group consisting of zeolite X, zeolite Y and USY.

6. The process of claim 1, wherein the large pore zeolite is partially or fully exchanged with a cation or cations selected from the rare-earth metals.

7. The process of claim 1, wherein the large pore zeolite comprises no more than 1.0 wt % sodium.

8. The process of claim 1, wherein the catalyst comprising the large pore zeolite further comprises a binder.

9. The process of claim 1, wherein a combination of metals is employed as the hydrogenation component.

10. The process of claim 9, wherein the combination of metals is selected from the group consisting of PdCu, PdZn, PdSn, PtSn, PtRe, NiW or CoMo.

* * * * *